United States Patent [19]
Bauer et al.

[11] Patent Number: 5,928,997
[45] Date of Patent: Jul. 27, 1999

[54] SYNERGISTIC HERBICIDAL AGENTS COMPRISING PHENOXYSULFONYLURE A HERBICIDES

[75] Inventors: Klaus Bauer, Hanau; Hermann Bieringer, Eppstein/Taunus; Erwin Hacker, Hochheim am Main, all of Germany

[73] Assignee: Hoechst Aktiengesellschaft, Frankfurt, Germany

[21] Appl. No.: 08/967,246

[22] Filed: Nov. 5, 1997

Related U.S. Application Data

[63] Continuation of application No. 07/852,166, filed as application No. PCT/EP90/01648, Oct. 1, 1990, abandoned.

[30] Foreign Application Priority Data

Oct. 7, 1989 [DE] Germany ............... 39 33 543

[51] Int. Cl.$^6$ .......... A01N 43/54; A01N 43/66; A01N 43/40; A01N 43/74
[52] U.S. Cl. .......... 504/133; 504/134; 504/136
[58] Field of Search .................. 504/136, 133, 504/134

[56] References Cited

U.S. PATENT DOCUMENTS

| | | | |
|---|---|---|---|
| 4,420,325 | 12/1983 | Sauers | 71/92 |
| 4,497,651 | 2/1985 | Hagen et al. | 71/94 |
| 4,840,663 | 6/1989 | Quadranti et al | 71/93 |
| 5,102,443 | 4/1992 | Kehne et al. | 71/92 |
| 5,104,443 | 4/1992 | Kehne et al. | 71/92 |

FOREIGN PATENT DOCUMENTS

| | | |
|---|---|---|
| 603232 | 1/1989 | Australia . |
| 0298901 | 1/1989 | European Pat. Off. . |
| 0298901 A3 | 1/1989 | European Pat. Off. . |
| 0303383 | 2/1989 | European Pat. Off. . |
| 0342568 | 11/1989 | European Pat. Off. . |
| 0342569 | 11/1989 | European Pat. Off. . |
| 0388771 | 9/1990 | European Pat. Off. . |
| 2609372 | 7/1988 | France . |
| 3108873 | 9/1982 | Germany . |
| 3108873 A1 | 9/1982 | Germany . |
| 61-5004 | 1/1986 | Japan . |
| 61-233605 | 10/1986 | Japan . |
| 62-84004 | 4/1987 | Japan . |
| 62-298505 | 12/1987 | Japan . |
| 90/2037 | 11/1990 | South Africa . |
| 8901289 | 2/1989 | WIPO . |
| WO 89/01289 | 2/1989 | WIPO . |

OTHER PUBLICATIONS

The Agrochemicals Handbook, $2^{nd}$ Edition, D. Hartley et al editors, Royal Society of Chemistry, UK, 1987, p. A573.
Japanese Abstract 61–233605, Herbicide Composition, vol. 11, No. 80.
Chemical Abstracts, vol. 101, 1984, p. 216.
Japanese Abstract 62–298505, Herbicide Composition for Paddy Field, vol. 12, No. 198, c 502.
Japanese Abstract 62–84004, Improved Herbicidal Granular Composition, vol. 11, No. 290, 77 c 447.
Japanese Abstract 61–5004, Mixed Herbicide, 131 c 349.
Japanese Abstract 58–185505, Herbicides, vol. 8, No. 19, c 207.
Japanese Abstract 58–185507, Herbicides, vol. 8, No. 19, c 207.

*Primary Examiner*—S. Mark Clardy
*Attorney, Agent, or Firm*—Frommer Lawrence & Haug LLP

[57] ABSTRACT

Increased synergistic herbicidal actions are obtained using combinations of the herbicides A and B, where A denotes substituted N-phenoxysulfonyl-N'-(4,6-disubstituted pyrimid-2-yl)ureas of the formula (I) as claimed in claim 1, and B denotes quinchlorac, molinate, thiobencarb, butachlor, pretilachlor, MON 7200, mefenacet, fenoxaprop-ethyl, dimepiperate and/or NTN-901.

15 Claims, No Drawings

SYNERGISTIC HERBICIDAL AGENTS COMPRISING PHENOXYSULFONYLUREA HERBICIDES

This application is a continuation of U.S. application Ser. No. 07/852,166, filed Apr. 3, 1992 abandoned, which was filed under 35 USC 371 as the national stage of PCT/EP90/01648, filed Oct. 1, 1990.

The invention is in the field of the plant protection agents which can be applied against monocotyledon and dicotyledon weeds.

German Patent Applications P 3,816,704.2 (EP-A-0,342,569), P 3,816,703.4 (EP-A-0,342,568) and P 3,909,053.1 (EP-A-0,388,771) describe heterocyclically substituted phenoxysulfonylureas by means of which a broad range of monocotyledon and dicotyledon weeds can be controlled. They can be applied as a soil-acting herbicide as well as via the leaves and also show a particularly high selectivity in monocotyledon plants such as cereals, maize, rice and sorghum.

However, there are a number of economically highly important monocotyledon weeds in cereals as well as in maize and rice, such as, for example, *Alopecurus myosuroides, Avena fatua, Echinochloa crus galli* or *Setaria viridis*, which cannot be controlled in an ideal manner by using the abovementioned compounds alone.

Surprisingly, biological tests have now revealed some herbicidal active substances which, when used together with the abovementioned compounds, have extremely synergistic properties as regards the effectiveness against weeds.

The present invention relates to herbicidal agents which contain an effective amount of (A) compounds of the formula (I) or salts thereof

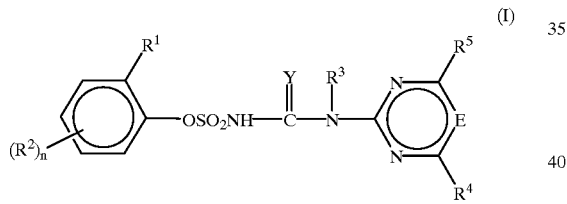

where a$_1$) $R^1$ is ethyl, propyl or isopropyl and
$R^2$ is halogen, $NO_2$, $CF_3$, CN, $C_1$–$C_4$-alkyl, $C_1$–$C_4$-alkoxy, $C_1$–$C_4$-alkylthio or ($C_1$–$C_4$-alkoxy)carbonyl and
n is 0, 1, 2 or 3, or a$_2$) $R^1$ is optionally unsaturated $C_1$–$C_8$-alkoxy, which is substituted by halogen, optionally unsaturated $C_1$–$C_6$-alkoxy, a radical of the formula ($C_1$–$C_6$-alkyl)—S—, ($C_1$–$C_6$-alkyl)—SO—, ($C_1$–$C_6$-alkyl)—SO$_2$—, ($C_1$–$C_6$-alkyl)—O—CO—, $NO_2$, CN or phenyl; furthermore $C_2$–$C_8$-alkenyloxy or -alkynyloxy and
$R^2$ is saturated or unsaturated $C_1$–$C_8$-alkyl, phenyl, phenoxy, $C_1$–$C_4$-alkoxy, $C_1$–$C_4$-alkylthio or ($C_1$–$C_4$-alkoxy)carbonyl, it being possible for all $R^2$ radicals above to be substituted by halogen, $C_1$–$C_4$-alkoxy or $C_1$–$C_4$-alkylthio, or is halogen, $NO_2$, $C_1$–$C_4$-alkylsulfonyl or -sulfinyl, and
n is 0, 1, 2 or 3, or a$_3$) $R^1$ is $C_1$–$C_8$-alkoxy and
$R^2$ is $C_2$–$C_8$-alkenyl or -alkynyl, phenyl or phenoxy, the $R^2$ radicals mentioned being unsubstituted or substituted by halogen, $C_1$–$C_4$-alkoxy or -alkylthio, or is $C_1$–$C_4$-alkylsulfonyl or -alkylsulfinyl, and n is 1, 2 or 3, or a$_4$) $R^1$—in each case in the 2-position of the phenyl radical—is halogen, methoxy, ethyl or propyl,
$R^2$ is ($C_1$–$C_4$-alkoxy)carbonyl in the 6-position in the phenyl radical and
n is 1 and, in all cases a$_1$)–a$_4$)

$R^3$ is hydrogen, saturated or unsaturated $C_1$–$C_8$-alkyl or $C_1$–$C_4$-alkoxy, $R^4$ and $R^5$ independently of one another are hydrogen, halogen, $C_1$–$C_4$-alkyl, $C_1$–$C_4$-alkoxy or $C_1$–$C_4$-alkylthio, the last three radicals mentioned being unsubstituted or substituted by halogen, $C_1$–$C_4$-alkoxy or $C_1$–$C_4$-alkylthio, Y is O or S, and E is CH or N in combination with B) one or more compounds from the group containing the compounds B1) 3,7-Dichloroquinoline-8-carboxylic acid and salts thereof,

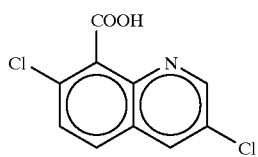

B2) N-(Ethylthiocarbonyl)azepane,

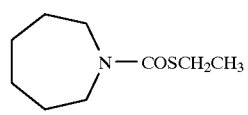

B3) N,N-Diethyl S-4-chlorobenzyl thiocarbamate,

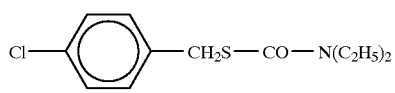

B4) N-(Butoxymethyl)-2-chloro-N-(2,6-diethylphenyl)-acetamide,

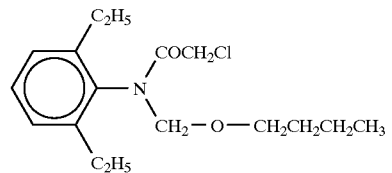

B5) N-(2-Propoxyethyl)-2-chloro-N-(2,6-diethylphenyl)-acetamide,

B6) 3,5-Bis(methylthiocarbonyl)-2-difluoromethyl-4-(2-methylpropyl)-6-trifluoromethylpyridine,

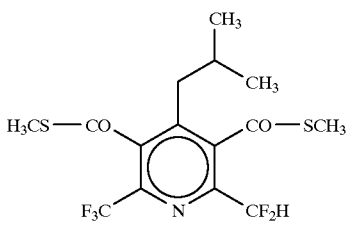

B7) 2-(1,3-Benzothiazol-2-yloxy)-N-methylacetanilide,

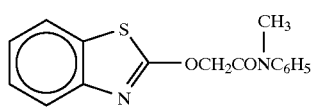

B8) Ethyl 2-[4-(6-chlorobenzoxazol-2-yloxy)phenoxy]propionate,

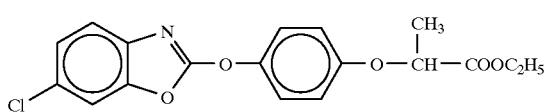

B9) N-(2-Phenylprop-2-ylthiocarbonyl)piperidine,

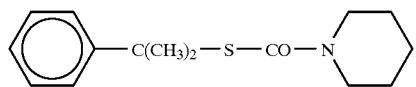

and

B10) NTN-901 (grass herbicide).

The compounds A (compounds of the formula I) are disclosed in the German Patent Applications mentioned at the beginning.

Compound B1 is known from British Crop Protection Conference—Weeds, 1985, pages 77–83 as BAS 514 H (quinchlorac).

Compounds B2–B5, B7 and B8 are all described in "The Pesticide Manual", British Crop Protection Council, 8th Ed., 1987; see B2 ("molinate") page 578; B3 ("thiobencarb") page 796; B4 ("butachlor") page 106; B5 ("pretilachlor") page 689; B7 ("mefenacet") page 526; B8 ("fenoxaprop-ethyl") page 379.

Compound B6 is known as "MON 7200" and described by M. Fujiyama, M. Kasai and S. Yamane in "Proceedings of the 11th Asian-Pacific Weed Science Society Conference 1987, page [sic] 455–460".

Compound B9 is described as a selective herbicide in "Short Review of Herbicides 1986", 5th Edition 1985, Hodogaya Chemical Co. Ltd., Japan, page 108 as MY-93 Kayamate, and in "Agricultural Chemicals Book II", Thomson Publications, USA 1989–90 as dimepiperate or yukamate. The compounds NTN-901, manufactured by Nihon Tokusho Nohyaku Seizo (Japan), is employed as a selective herbicide for controlling Echinochloa in rice.

Herbicidal agents according to the invention which are of particular interest are those containing compounds of the abovementioned formula (I) or salts thereof, where a$_1$) R$^1$ is ethoxy, propoxy or isopropoxy and
R$^2$ is orientated in the 6-position and has the above-mentioned meaning, and
n is 0 or 1, or a$_2$) R$^1$ is optionally unsaturated C$_1$–C$_4$-alkoxy, which is substituted by halogen, C$_1$–C$_4$-alkoxy, C$_1$–C$_4$-alkylthio or -sulfinyl or -sulfonyl, (C$_1$–C$_4$)alkoxycarbonyl, NO$_2$, CN or phenyl; furthermore is C$_2$–C$_5$-alkenyloxy or C$_2$–C$_4$-alkynyloxy, and
R$^2$ is C$_1$–C$_4$-alkyl, C$_2$–C$_5$-alkenyl, (C$_1$–C$_4$-alkoxy)-carbonyl, C$_1$–C$_4$-alkoxy or C$_1$–C$_4$-alkylthio, each of which can be substituted as indicated above, or is halogen, and
n is 0 or 1, or a$_3$) R$^1$ is methoxy, ethyl or propyl and
R$^2$ is 6-methoxycarbonyl or 6-ethoxycarbonyl, and
n is 1, and also in all cases a$_1$)–a$_3$)
R$^3$ is hydrogen, C$_1$–C$_4$-alkyl, in particular hydrogen or methyl,
R$^4$ and R$^5$ are halogen, C$_1$–C$_4$-alkyl, C$_1$–C$_4$-alkoxy or C$_1$–C$_4$-alkylthio, the last 3 radicals mentioned being unsubstituted or substituted by halogen, C$_1$–C$_4$-alkoxy or C$_1$–C$_4$-alkylthio,
Y is O or S, in particular O, and
E is CH or N, in particular CH.

Saturated or unsaturated alkyl and alkoxy are, correspondingly, straight-chain or branched alkyl or alkoxy, halogen is F, Cl, Br and I, preferably F and Cl.

The compounds of the formula (1) can form salts in which the hydrogen of the —SO$_2$—NH group is replaced by a cation which is suitable for agriculture. These salts are generally metal salts, in particular alkali metal salts, alkaline earth metal salts, and, if appropriate, alkylated ammonium salts or organic amine salts.

The stereochemistry in the abovementioned formulae of the compounds A and B was not indicated in detail. Where stereoisomers may occur, the formulae also comprise all geometric isomers, enantiomers and diastereomers, as well as their mixtures. In the case of the compound B8, D-fenoxaprop-ethyl, in particular, is also embraced and preferred.

Preferred herbicidal agents contain one or more compounds of the formulae A1, A2 and A3 as compounds A, the formulae having the following meaning:

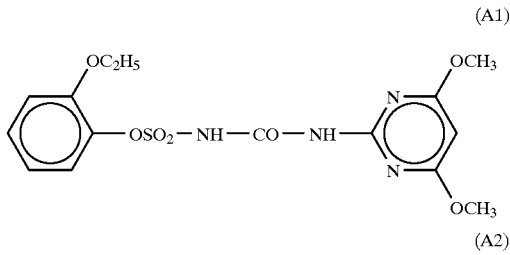

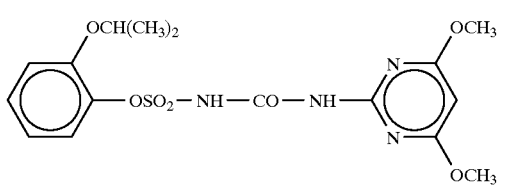

-continued (A3)

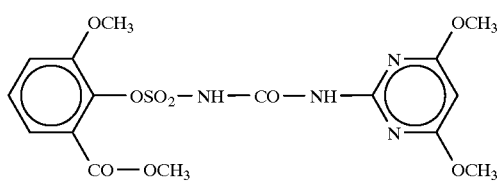

The herbicidal agents according to the invention have an excellent herbicidal activity against a broad range of economically important monocotyledon and dicotyledon harmful plants. The active substance combinations also act efficiently on perennial weeds which produce shoots from rhizomes, rootstocks or other perennial organs and which are difficult to control. In this context, it does not matter whether the substances are applied before sowing, pre-emergence or post-emergence. Specifically, examples may be mentioned of some representatives of the monocotyledon and dicotyledon weed flora which can be controlled by the agents according to the invention, without the enumeration being a restriction to certain species.

Examples of weed species on which the active substance acts efficiently are, from amongst the monocotyledons, Avena, Lolium, Alopecurus, Phalaris, Echinochloa, Digitaria, Setaria and also Cyperus species from the annual sector and from amongst the perennial species Agropyron, Cynodon, Imperata and Sorghum, and also perennial Cyperus species.

In the case of the dicotyledon weed species, the range of action extends to Galium, Viola, Veronica, Lamium, Stellaria, Amaranthus, Sinapis, Ipomoea, Matricaria, Abutilon, Sida, etcetera from amongst the annuals, and Convolvulus, Cirsium, Rumex, Artemisia etc. in the case of the perennial weeds.

The active substance combinations according to the invention likewise effect outstanding control of weeds which occur under the specific conditions of rice growing, such as, for example, Sagittaria, Alisma, Eleocharis, Scirpus, Cyperus etc.

Under the specific conditions of maize and rice growing, control is also effected on economically important monocotyledon weeds such as, for example, *Alopecurus myosuroides, Avena fatua, Echinochloa crus galli* and *Setaria viridis.*

If the herbicidal agents according to the invention are applied to the soil surface before germination, then the weed seedlings are either completely prevented from emerging, or the weeds grow until they have reached the cotyledon stage but then their growth stops, and, eventually, after three to four weeks have elapsed, they die completely.

If the active substance combinations are applied post-emergence to the green parts of the plants, growth likewise stops drastically a very short time after the treatment and the weed plants remain at the growth stage of the point of time of application, or they die more or less quickly after a certain time, so that in this manner competition by the weeds, which is harmful to the crop plants, is eliminated at a very early point in time and in a sustained manner by employing the novel agents according to the invention.

Even though the agents according to the invention have an excellent herbicidal activity against monocotyledon and dicotyledon weeds, crop plants of economically important crops, such as, for example, wheat, barley, rye, rice and maize, are damaged not at all, or only to a negligible extent.

For these reasons, the agents are highly suitable for selectively controlling undesired plant growth in plantings for agricultural use.

For example, a herbicidal action is achieved using the active substance combinations according to the invention which exceeds what would have been expected as an additive action of the individual components. Such increased actions permit considerable reduction of the amounts of the individual active substances applied. Advantages as regards the action were also found of a nature such that either the long-term action of the combinations is improved, or that an increased speed of action can be observed. Such properties are therefore novel inventions which are economically advanced and which offer considerable advantages to the user in practical weed control by enabling him to control weeds in a more cost-effective, or rapid, or sustainable, manner and hence to harvest a higher yield of a given crop.

Furthermore, it has been found that there is a pronounced safener or antidote action in a number of the active substance combinations, i.e., that phytotoxic side-effects of the active substances used in crop plants such as, for example, rice, are reduced or avoided completely.

The mixing ratios A:B can vary within wide limits and are generally between 1:0.5 to 1:200. The mixing ratio is selected for example as a function of the other substance in the mixture, the stage of development of the weeds, the weed spectrum and the climatic conditions.

It is preferred to use mixing ratios of 1:1 to 1:100. The application rates of herbicide A in the active substance mixtures are preferably between 10 and 100 g/ha, application rates of B between 0.02 and 4.0 kg/ha.

The active substance combinations according to the invention can be either in the form of mixed formulations of the two components which are then applied in a customary manner as a dilution with water, or in the form of so-called tank mixes which can be prepared by joint dilution with water of the components which are formulated separately.

The compounds A and B or their combinations can be formulated in a variety of ways, as predetermined by the biological and/or chemicophysical parameters. The following possibilities are suitable for formulation for example: wettable powders (WP), emulsifiable concentrates (EC), aqueous solutions (SL), emulsions (EW) such as oil-in-water and water-in-oil emulsions, sprayable solutions or emulsions, dispersions on an oil or water base, suspoemulsions, dusting agents (DP), seed-dressing agents, granules for soil application or for broadcasting or water-dispersible granules (WG), ULV formulations, microcapsules or waxes.

These individual formulation types are known in principle and are described, for example, in: Winnacker-Küchler, "Chemische Technologie [Chemical Technology]", Volume 7, C. Hauser Verlag Munich, 4th Ed., 1986; van Valkenburg, "Pesticides Formulations", Marcel Dekker N.Y., 2nd Ed. 1972–73; K. Martens, "Spray Drying Handbook", 3rd Ed. 1979, G. Goodwin Ltd. London.

The formulation auxiliaries required, such as inert materials, surfactants, solvents and other additives, are likewise known and are described, for example, in: Watkins, "Handbook of Insecticide Dust Diluents and Carriers", 2nd Ed., Darland Books, Caldwell N.J.; H. v. Olphen, "Introduction to Clay Colloid Chemistry"; 2nd Ed., J. Wiley & Sons, N.Y.; Marsden, "Solvents Guide", 2nd Ed., Interscience, N.Y. 1950; McCutcheon's, "Detergents and Emulsifiers Annual", MC Publ. Corp., Ridgewood N.J.; Sisley and Wood, "Encyclopedia of Surface Active Agents", Chem. Publ. Co. Inc., N.Y. 1964; Schönfeldt, "Grenzfl ächenaktive Äthylenoxidaddukte" [Surface-active Ethylene Oxide Adducts]", Wiss. Verlagsgesell., Stuttgart 1976, Winnacker-Küchler, "Chemische Technologie [Chemical Technology]", Volume 7, C. Hauser Verlag Munich, 4th Ed. 1986.

Combinations with other pesticidally active substances, such as other herbicides, fungicides or insecticides, and also fertilizers and/or growth regulators may also be prepared on the basis of these formulations, for example in the form of a readymix or as a tank mix.

Wettable powders are preparations which are uniformly dispersible in water and which, besides the active substance, also contain wetting agents, for example polyoxethylated alkylphenols, polyoxethylated fatty alcohols or fatty amines, alkane- or alkylbenzenesulfonate [sic], and dispersing agents, for example sodium ligninsulfonate, sodium 2,2'-dinaphthylmethane-6,6'-disulfonate, sodium dibutylnaphthalenesulfonate, or alternatively sodium oleylmethyltaurinate, in addition to a diluent or inert substance.

Emulsifiable concentrates are prepared by dissolving the active substance in an organic solvent, for example butanol, cyclohexanone, dimethylformamide, xylene and also higher-boiling aromatic compounds or hydrocarbons, with the addition of one or more emulsifiers. Examples of emulsifiers which can be used are: calcium salts of an alkylarylsulfonic acid, such as Ca dodecylbenzenesulfonate, or non-ionic emulsifiers, such as fatty acid polyglycol esters, alkylaryl polyglycol ethers, fatty alcohol polyglycol ethers, propylene oxide/ethylene oxide condensation products, alkyl polyethers, sorbitan fatty acid esters, polyoxyethylene sorbitan fatty acid esters or polyoxyethylene sorbitol esters.

Dusting agents can be obtained by grinding the active substance with finely divided solid substances, for example talc or natural clays, such as kaolin, bentonite, pyrophyllite or diatomaceous earth.

Granules can be produced either by spraying the active substance onto adsorptive, granulated inert material or by applying active substance concentrates onto the surface of carriers, such as sand, kaolinites or granulated inert material, by means of binders, for example polyvinyl alcohol, sodium polyacrylate or, alternatively, mineral oils. Suitable active substances can also be granulated in the manner which is conventional for the production of fertilizer granules, if desired in a mixture with fertilizers.

The agrochemical preparations generally contain 0.1 to 99 percent by weight, in particular 2 to 95% by weight, of active substances A+B. The concentrations of the active substances A+B can differ in the formulations.

The concentration of active substance in wettable powders is, for example, about 10 to 95% by weight; the remainder to 100% by weight is composed of conventional formulation components. In the case of emulsifiable concentrates, the concentration of active substance can be about 1 to 85% by weight, preferably 5 to 80% by weight. Formulations in the form of dusts contain about 1 to 25% by weight, usually 5 to 20% by weight of active substance, sprayable solutions about 0.2 to 25% by weight, preferably 2 to 20% by weight of active substance. In the case of granules, such as water-dispersible granules, the active substance content depends partly on whether the active compound is liquid or solid and on which granulation auxiliaries, fillers etc. are used. In the case of water-dispersible granules the content is generally between 10 and 90% by weight.

In addition, the active substance formulations mentioned contain, if appropriate, the adhesives, wetting agents, dispersing agents, emulsifiers, penetrants, solvents, fillers or carriers which are conventional in each case.

For use, the formulations, present in commercially available form, are diluted, if appropriate, in a customary manner, for example using water in the case of wettable powders, emulsifiable concentrates, dispersions and water-dispersible granules. Preparations in the form of dusts, soil granules or granules for broadcasting and also sprayable solutions are usually not further diluted with other inert substances before use.

The application rate required for the compounds of the formula (I) varies with the external conditions, such as, inter alia, temperature, humidity, and the nature of the herbicide used.

The examples which follow serve to illustrate the invention:

A. FORMULATION EXAMPLES a) A dusting agent is obtained by mixing 10 parts by weight of an active substance combination according to the invention and 90 parts by weight of talc as inert substance and comminuting the mixture in a hammer mill.

b) A wettable powder which is readily dispersible in water is obtained by mixing 25 parts by weight of active substance A+B, 64 parts by weight of kaolin-containing quartz as the inert substance, 10 parts by weight of potassium ligninsulfonate and 1 part by weight of sodium oleoylmethyltaurinate as the wetting and dispersing agent, and grinding the mixture in a pinned disk mill.

c) A dispersion concentrate which is readily dispersible in water is obtained by mixing 20 parts by weight of active substance A+B with 6 parts by weight of alkylphenol polyglycol ether (®Triton X 207), 3 parts by weight of isotridecanol polyglycol ether (8 EO) and 71 parts by weight of paraffinic mineral oil (boiling range, for example, about 255 to above 277° C.), and grinding the mixture in a ball mill to a fineness of below 5 microns.

d) An emulsifiable concentrate is obtained from 15 parts by weight of active substance A+B, 75 parts by weight of cyclohexanone as the solvent and 10 parts by weight of oxethylated nonylphenol as the emulsifier.

e) Water-dispersible granules are obtained by mixing 75 parts by weight of active substances A + B,
10 parts by weight of calcium ligninsulfonate,
5 parts by weight of sodium lauryl sulfate,
3 parts by weight of polyvinyl alcohol and
7 parts by weight of of kaolin, grinding the mixture on a pinned disk-mill, and granulating the powder in a fluidized bed by spraying on water as the granulation liquid.

f) Water-dispersible granules are also obtained by homogenizing and precomminuting, on a colloid mill, 25 parts by weight of active substances A + B,
5 parts by weight of sodium 2,2'-dinaphthyl-
    methane-6,6'disulfonate,
2 parts by weight of sodium oleoylmethyltaurinate,
1 parts by weight of polyvinyl alcohol,
17 parts by weight of calcium carbonate and
50 parts by weight of water, subsequently grinding the mixture on a bead mill, and atomizing and drying the resulting suspension in a spray tower by means of a single-fluid nozzle.

The formulations described under a) to f) are used for formulating, for example, the active substance combinations in Table 1 below:

TABLE 1

| Active substance A | Active-substance B | Ratio |
|---|---|---|
| A1 | B1 | 1:2 |
|  |  | 1:10 |
|  |  | 1:100 |
| A1 | B2 | 1:2 |
|  |  | 1:10 |
|  |  | 1:100 |
| A1 | B3 | 1:2 |
|  |  | 1:10 |
|  |  | 1:100 |
| A1 | B4 | 1:2 |
|  |  | 1:10 |
|  |  | 1:100 |
| A1 | B5 | 1:2 |
|  |  | 1:10 |
|  |  | 1:100 |
| A1 | B6 | 1:2 |
|  |  | 1:10 |
|  |  | 1:150 |
| A1 | B7 | 1:2 |
|  |  | 1:10 |
|  |  | 1:150 |
| A1 | B8 | 1:2 |
|  |  | 1:10 |
|  |  | 1:150 |
| A2 | B1 | 1:2 |
|  |  | 1:10 |
|  |  | 1:100 |
| A2 | B2 | 1:2 |
|  |  | 1:10 |
|  |  | 1:100 |
| A2 | B3 | 1:2 |
|  |  | 1:10 |
|  |  | 1:100 |
| A2 | B4 | 1:2 |
|  |  | 1:10 |
|  |  | 1:100 |
| A2 | B5 | 1:2 |
|  |  | 1:10 |
|  |  | 1:100 |
| A2 | B6 | 1:2 |
|  |  | 1:10 |
|  |  | 1:150 |
| A2 | B7 | 1:2 |
|  |  | 1:10 |
|  |  | 1:150 |
| A2 | B8 | 1:2 |
|  |  | 1:10 |
|  |  | 1:150 |
| A3 | B1 | 1:2 |
|  |  | 1:10 |
|  |  | 1:100 |
| A3 | B2 | 1:2 |
|  |  | 1:10 |
|  |  | 1:100 |
| A3 | B3 | 1:2 |
|  |  | 1:10 |
|  |  | 1:100 |
| A3 | B4 | 1:2 |
|  |  | 1:10 |
|  |  | 1:100 |
| A3 | B5 | 1:2 |
|  |  | 1:10 |
|  |  | 1:100 |
| A3 | B6 | 1:2 |
|  |  | 1:10 |
|  |  | 1:150 |
| A3 | B7 | 1:2 |
|  |  | 1:10 |
|  |  | 1:150 |
| A3 | B8 | 1:2 |
|  |  | 1:10 |
|  |  | 1:150 |

BIOLOGICAL EXAMPLES

1. Pre-emergence effect on weeds

Seeds or rhizome pieces of monocotyledon and dicotyledon weed plants are placed in sandy loam soil in plastic pots of diameter 9 cm and covered with soil. The weeds which occur in rice growing are grown in water-saturated soil, for which purpose such an amount of water is added to the pots that it reaches the soil surface, or rises a few millimeters above. The active substance combinations according to the invention which were formulated in the form of wettable powders or emulsion concentrates, and, in parallel trials, the appropriately formulated individual active substances, are then applied to the surface of the soil cover in the form of aqueous suspensions or emulsions at an application rate of 600 to 800 l of water/ha (converted), in various dosages, or, in the case of rice, poured into the irrigation water.

After the treatment, the pots are placed in a greenhouse and kept under good growth conditions for the weeds. After the test plants had emerged, the damage to the plants or the negative effect on the emergence was scored visually after a test period of 3 to 4 weeks by comparison with untreated controls. The herbicidal agents according to the invention have a good herbicidal pre-emergence action against a broad range of grass weeds and dicotyledon weeds.

In the combinations, differences were found in all cases between the calculated and the found degree of effectiveness. The calculated degree of effectiveness of a combination which is to be expected according to theory is determined using S. R. Colby's formula: Calculation of synergistic and antagonistic responses of herbicide combinations, Weeds 15 (1967) 20–22.

This formula is:

$$E = X + Y - \frac{X \cdot Y}{100}$$

where

X=% damage by herbicide A at an application rate of x kg/ha;

Y=% damage by herbicide B at an application rate of y kg/ha;

E=expected damage by the herbicides A+B when applying x+y kg/ha.

If the actual damage is greater than the damage to be expected by calculations, then the action of the combination is superadditive, i.e., there is a synergistic effect of action.

The active substance combinations according to the invention have a herbicidal action which is higher than to be expected, according to Colby, on the basis of the observed actions of the individual components when they are used alone. The active substance combinations are therefore synergistic (cf. Table 2).

TABLE 2

| | | Pre-emergence application | | | |
|---|---|---|---|---|---|
| | | | % herbicidal action on | | |
| Herbicide(s) | Dose | Transplanted rice | Sown rice | ECCG | CYMO |
| A1 | 20 | 15 | 30 | 75 | 99 |
|  | 5 | 10 | 10 | 30 | 50 |
|  | 1.25 | 0 | 0 | 0 | 0 |
| B8 | 120 | 10 | 75 | 100 | 10 |

TABLE 2-continued

Pre-emergence application

% herbicidal action on

| Herbi-cide(s) | Dose | Trans-planted rice | Sown rice | ECCG | | CYMO | |
|---|---|---|---|---|---|---|---|
| | 30 | 0 | 5 | 30 | | 0 | |
| | 8 | 0 | 0 | 0 | | 0 | |
| A1 + | 20 + 120 | 10 | 65 | 100 | (100) | 100 | (99) |
| B8 | 5 + 30 | 0 | 5 | 185 | (51) | 95 | (50) |
| | 1 + 8 | 0 | 0 | 40 | (0) | 25 | (0) |
| B3 | 250 | 0 | 25 | 75 | | 35 | |
| | 60 | 0 | 0 | 20 | | 0 | |
| | 15 | 0 | 0 | 0 | | 0 | |
| A1 + | 20 + 250 | 15 | 40 | 95 | (94) | 100 | (99) |
| B3 | 20 + 60 | 5 | 20 | 90 | (80) | 100 | (99) |
| | 5 + 250 | 5 | 25 | 90 | (83) | 90 | (68) |
| | 6 + 60 | 0 | 5 | 65 | (44) | 85 | (50) |
| B9 | 200 | 5 | 25 | 93 | | 0 | |
| | 50 | 0 | 10 | 25 | | 0 | |
| | 12 | 0 | 0 | 0 | | 0 | |
| A1 + | 20 + 50 | 0 | 20 | 90 | (81) | 99 | (99) |
| B9 | 5 + 50 | 0 | 10 | 75 | (48) | 95 | (50) |
| | 5 + 12 | 0 | 0 | 60 | (30) | 75 | (50) |

Abbreviations:
ECCG = *Echinochloa crus galli*;
CYMO = *Cyperus monti* = *Cyperus serotinus*
AI = active ingredient (based on pure active substance)
( ) = expected value, using Colby's formula
A1 = 1-(4,6-dimethoxypyrimid-2-yl)-3-[(2-ethoxyphenoxy)sulfonyl]urea
B3 = thiobencarb
B8 = fenoxaprop-ethyl
B9 = dimepiperate 2. Post-emergence effect on weeds Seeds or rhizome pieces of monocotyledon and dicotyledon weeds are placed in sandy loam soil in plastic pots, covered with soil and grown in a greenhouse under good growth conditions. Weeds which occur in rice growing are grown in pots in which the water floods the soil surface by up to 2 cm, and cultivated during the test phase. Three weeks after sowing, the test plants are treated in the three-leaf stage.

The active substance combinations according to the invention which are formulated as wettable powders or as emulsion concentrates, and, in parallel trials, the appropriately formulated individual active substances, are sprayed in various dosages on the green parts of the plants at an application rate of 300 to 600 l of water/ha (converted) and, after the test plants had remained in the greenhouse for about 3 to 4 weeks under ideal growth conditions, the effect of the preparations is scored visually by comparison with untreated controls. In the case of weeds which occur in rice growing, the active substances are also added directly to the irrigation water (application in analogy to so-called granule application), or sprayed onto plants and into the irrigation water. The agents according to the invention also have a good herbicidal post-emergence action against a broad range of economically important grass weeds and dicotyledon weeds. According to Colby analysis (cf. Biological Example 1), the effects of the agents according to the invention are synergistic (see Table 3).

TABLE 3

Post-emergence application

Pre-emergence application

% herbicidal action on

| Herbi-cide(s) | Dose | Trans-planted rice | Sown rice | ECCG | | CYMO | |
|---|---|---|---|---|---|---|---|
| A1 | 20 | 0 | 0 | 30 | | 70 | |
| | 5 | 0 | 0 | 0 | | 30 | |
| | 1.25 | 0 | 0 | 0 | | 10 | |
| B1 | 250 | 0 | 0 | 97 | | 0 | |
| | 60 | 0 | 0 | 70 | | 0 | |
| | 15 | 0 | 0 | 0 | | 0 | |
| A1 + | 20 + 250 | 0 | 0 | 99 | (98) | 85 | (70) |
| B1 | 5 + 60 | 0 | 0 | 90 | (70) | 75 | (30) |
| | 1 + 15 | 0 | 0 | 50 | (0) | 40 | (10) |
| B2 | 1,000 | 0 | 10 | 90 | | 75 | |
| | 250 | 0 | 0 | 48 | | 45 | |
| | 60 | 0 | 0 | 0 | | 10 | |
| A1 + | 20 + 250 | 0 | 0 | 85 | (64) | 99 | (84) |
| B2 | 20 + 60 | 0 | 0 | 60 | (48) | 90 | (73) |
| | 5 + 250 | 0 | 0 | 70 | (0) | 85 | (62) |
| | 5 + 60 | 0 | 0 | 45 | (0) | 55 | (37) |
| | 1 + 60 | 0 | 0 | 30 | (0) | 40 | (19) |
| B4 | 300 | 0 | 0 | 85 | | 0 | |
| | 80 | 0 | 0 | 50 | | 0 | |
| | 20 | 0 | 0 | 0 | | 0 | |
| A1 + | 20 + 80 | 0 | 0 | 75 | (65) | 90 | (70) |
| B4 | 5 + 80 | 0 | 0 | 70 | (50) | 80 | (30) |
| | 5 + 20 | 0 | 0 | 50 | (0) | 75 | (10) |

Abbreviations:
ECCG = *Echinochloa crus galli*;
CYMO = *Cyprerus monti* = *Cyperus serotinus*
AI = active ingredient (based on pure active substance)
( ) = expected value, using Colby's formula
A1 = 1-(4,6-dimethoxypyrimid-2-yl)-3-[(2-ethoxyphenoxy)sulfonyl]urea
B3 = quinchlorac
B8 = molinate
B9 = butachlor 3. Tolerance by crop plants In further greenhouse experiments seeds of a substantial number of crop plants and weeds were placed in sandy loam soil and covered with soil. Rice is grown as paddy rice in water-saturated soil and cultivated.

Some of the pots are treated immediately as described under 1., and the remaining pots are placed in a greenhouse until the plants have developed two to three true leaves, and are then sprayed with various dosages, as described under 2., of the active substance combinations according to the invention and for comparison reasons only with one individual active substance. In the case of paddy rice, the application is also carried out in some cases by pouring the active substances or their formulation into the irrigation water.

Visual scoring four to five weeks after the application and after the plants have been in the greenhouse reveals that pre-emergence and post-emergence application of the active substance combinations according to the invention does not inflict any damage to various cultures, even when high doses of active substance are applied. They leave Gramineae crops such as, for example, barley, wheat, rye, sorghum species and, in particular, maize and rice unharmed (see also Tables 2 and 3, columns 3 and 4). The active substance combinations according to the invention therefore have a high selectivity when used for controlling undesired plant growth in agricultural crops.

Compared with the use of the individual active substances alone, it is also particularly obvious at increased dosages that the selectivity of the active substance combinations, compared with the individual active substances at the same application rate of the most effective herbicide in each case, is better. The active substance combinations are therefore suitable for effectively reducing herbicide damage on crop plants.

We claim:
1. A herbicidal agent which comprises an effective amount of

(A) compounds of the formula (I) or salts thereof

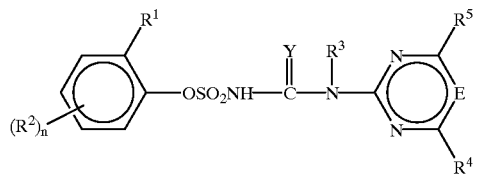

where
a₁) $R^1$ is ethoxy, propoxy or isopropoxy and
$R^2$ is halogen, $NO_2$, $CF_3$, CN, $C_1$–$C_4$-alkyl, $C_1$–$C_4$-alkoxy, $C_1$–$C_4$-alkylthio or ($C_1$–$C_4$-alkoxy)carbonyl and
n is 0, 1, 2 or 3, or
a₂) $R^1$ is optionally unsaturated $C_1$–$C_8$-alkoxy, which is substituted by halogen, optionally unsaturated $C_1$–$C_6$-alkoxy, a radical of the formula ($C_1$–$C_6$-alkyl)—S—, ($C_1$–$C_6$-alkyl)—SO—, ($C_1$–$C_6$-alkyl)—SO₂—, ($C_1$–$C_6$-alkyl)—O—CO—, $NO_2$, CN or phenyl; furthermore $C_2$–$C_8$-alkenyloxy or -alkynyloxy and
$R^2$ is saturated or unsaturated $C_1$–$C_8$-alkyl, phenyl, phenoxy, $C_1$–$C_4$-alkoxy, $C_1$–$C_4$-alkylthio or ($C_1$–$C_4$-alkoxy)carbonyl, it being possible for all $R^2$ radicals above to be substituted by halogen, $C_1$–$C_4$-alkoxy or $C_1$–$C_4$-alkylthio, or is halogen, $NO_2$, $C_1$–$C_4$-alkylsulfonyl or -sulfinyl, and
n is 0, 1, 2 or 3, or
a₃) $R^1$ is $C_1$–$C_8$-alkoxy and
$R^2$ is $C_2$–$C_8$-alkenyl or -alkynyl, phenyl or phenoxy, the $R^2$ radicals mentioned being unsubstituted or substituted by halogen, $C_1$–$C_4$-alkoxy or -alkylthio, or is $C_1$–$C_4$-alkylsulfonyl or -alkylsulfinyl, and
n is 1, 2 or 3, or
a₄) $R^1$—in each case in the 2-position of the phenyl radical—is halogen, methoxy, ethyl or propyl,
$R^2$ is ($C_1$–$C_4$-alkoxy)carbonyl in the 6-position in the phenyl radical and
n is 1
and, in all cases a₁)–a₄)
$R^3$ is hydrogen, saturated or unsaturated $C_1$–$C_8$-alkyl or $C_1$–$C_4$-alkoxy,
$R^4$ and $R^5$ independently of one another are hydrogen, halogen, $C_1$–$C_4$-alkyl, $C_1$–$C_4$-alkoxy or $C_1$–$C_4$-alkylthio, the last three radicals mentioned being unsubstituted or substituted by halogen, $C_1$–$C_4$-alkoxy or $C_1$–$C_4$-alkylthio,
Y is O or S, and
E is CH or N
in combination with
B) one or more compounds from the group containing the compounds
B1) 3,7-Dichloroquinoline-8-carboxylic acid and salts thereof,

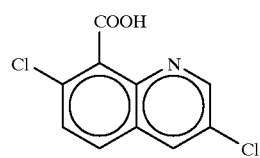

B2) N-(Ethylthiocarbonyl)azepane,

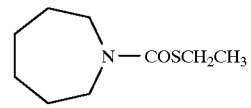

B3) N,N-Diethyl S-4-chlorobenzyl thiocarbamate,

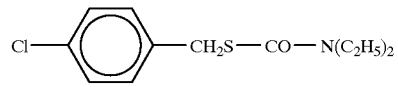

B4) N-(Butoxymethyl)-2-chloro-N-(2,6-diethylphenyl) acetamide,

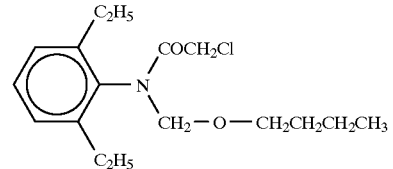

B5) N-(2-Propoxyethyl)-2-chloro-N-(2,6-diethylphenyl) acetamide,
B6) 3,5-Bis(methylthiocarbonyl)-2-difluoromethyl-4-(2-methylpropyl)-6-trifluoromethylpyridine,

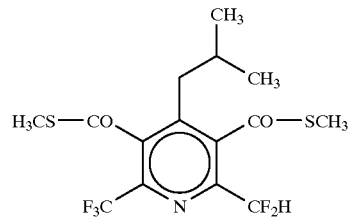

B7) 2-(1,3-Benzothiazol-2-yloxy)-N-methylacetanilide,

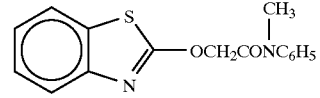

B8) Ethyl 2-[4-(6-chlorobenzoxazol-2-yloxy) phenoxy] propionate,

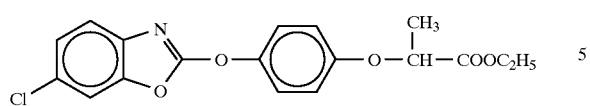
(B8)

B9) N-(2-Phenylprop-2-ylthiocarbonyl)piperidine,

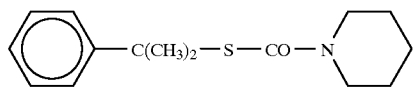
(B9)

and

B10) NTN-901 (grass herbicide).

2. The agent as claimed in claim 1, which comprises compounds of the formula (I) or salts thereof, where $a_1$) $R^1$ is ethoxy, propoxy or isopropoxy and
  $R^2$ is orientated in the 6-position and has the above-mentioned meaning, and
  n is 0 or 1, or $a_2$) $R^1$ is optionally unsaturated $C_1$–$C_4$-alkoxy, which is substituted by halogen, $C_1$–$C_4$-alkoxy, $C_1$–$C_4$-alkylthio or -sulfinyl or -sulfonyl, ($C_1$–$C_4$) alkoxycarbonyl, $NO_2$, CN or phenyl; furthermore is $C_2$–$C_5$-alkenyloxy or $C_2$–$C_4$-alkynyloxy, and
  $R^2$ is $C_1$–$C_4$-alkyl, $C_2$–$C_5$-alkenyl, ($C_1$–$C_4$-alkoxy) carbonyl, $C_1$–$C_4$-alkoxy or $C_1$–$C_4$-alkylthio, each of which can be substituted as indicated above, or is halogen, and
  n is 0 or 1, or $a_3$) $R^1$ is methoxy, ethyl or propyl and
  $R_2$ is 6-methoxycarbonyl or 6-ethoxycarbonyl and
  n is 1, and also
  in all cases $a_1$)–$a_3$)
  $R^3$ is hydrogen, $C_1$–$C_4$-alkyl,
  $R^4$ and $R^5$ are halogen, $C_1$–$C_4$-alkyl, $C_1$–$C_4$-alkoxy or $C_1$–$C_4$-alkylthio, the last 3 radicals mentioned being unsubstituted or substituted by halogen, $C_1$–$C_4$-alkoxy or $C_1$–$C_4$-alkylthio,
  Y is O or S, and
  E is CH or N.

3. The agent as claimed in claim 1, which comprises one or more compounds of the formulae A1, A2 and A3 or salts thereof

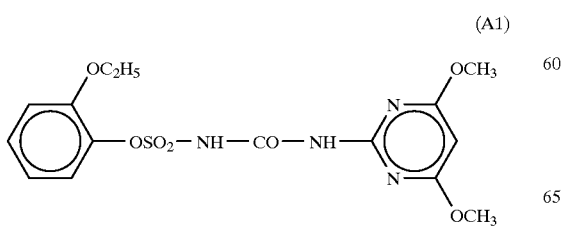
(A1)

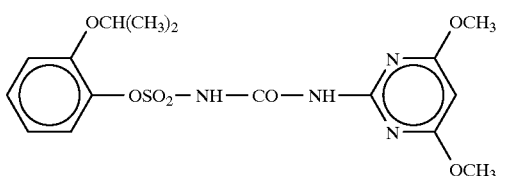
(A2)

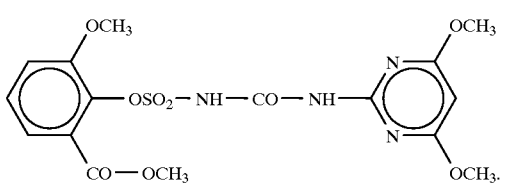
(A3)

4. The agent as claimed in claim 1 which comprises, besides conventional formulation auxiliaries, 0.1 to 99% by weight of the active substances A and B.

5. The agent as claimed in claim 1 which comprises the active substances A and B in a ratio by weight of 2:1 to 1:200.

6. The agent as claimed in claim 1, which comprises the compound of the formula A1, or salts thereof:

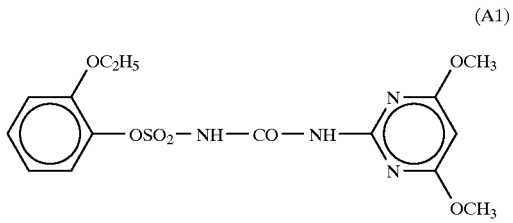
(A1)

in combination with a compound of the formula B3 N,N-Diethyl S-4-chlorobenzyl thiocarbamate,

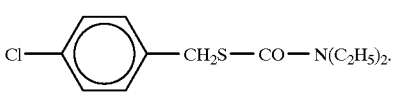
(B3)

7. The agent as claimed in claim 6, where the active substance A and B are in a ratio by weight of 6:60.

8. The agent as claimed in claim 1, which comprises a synergistically effective amount of A) a compound or a salt thereof selected from the group consisting of:

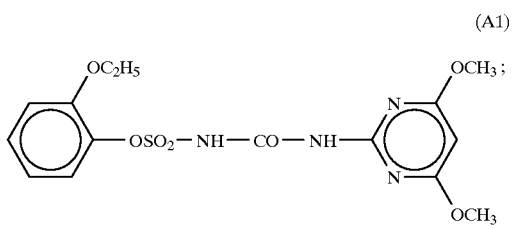
(A1)

(A2)

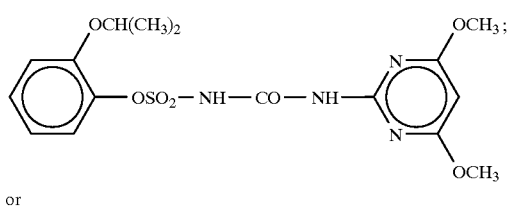

or (A3)

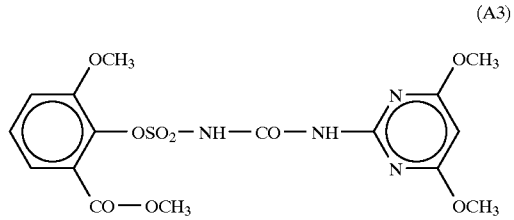

in combination with

B) N, N-diethyl S-4-chlorobenzyl thiocarbonate (B3)

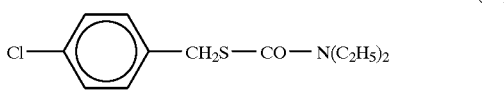

wherein the active substance, A and B, are in a ratio by weight of 2:1 to 1:200.

9. A herbicidal agent, which comprises an effective amount of
   A) compounds of the formula (I) or their salts, as are defined in one of claims 1 to 3 in combination with
   B) one or two compounds from the group which contains the compounds
      B6) 3,5-bis(methylthiocarbonyl)-2-difluoromethyl-4-(2-methylpropyl-6-trifluoromethylpyridine of the formula (B6)

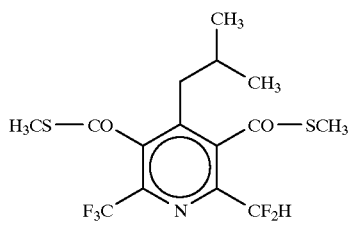

and
   B10) NTN-901 (grass herbicide).
10. A herbicidal agent as claimed in one of claims 1 to 5, wherein the compound B is from the group comprising
    B7) 2-(1,3-benzothiazol-2-yloxy)-N-methylacetanilide, and
    B8) ethyl 2-[4-(6-chlorobenzoxazol-2-yloxy) phenoxy] propionate.
11. A herbicidal agent as claimed in one of claims 1–5, wherein the compound B is
    B7) 2-(1,3-benzothiazol-2-yloxy)-N-methylacetanilide.
12. A process for the preparation of an agent as claimed in claim 1, which comprises formulating one or more compounds A with one or more compounds B analogously to a conventional formulation for plant protection agents from the group containing wettable powders, emulsifiable concentrates, aqueous solutions, emulsions, sprayable solutions (tank mix), dispersions on an oil or water base, suspoemulsions, dusting agents, seed-dressing agents, soil granules or granules for broadcasting, water-dispersible granules, ULV formulations, microcapsules and waxes.
13. A method for controlling undesired plants, which comprises the application of a herbicidally effective amount of an agent as claimed in claim 1 to these plants or the areas under cultivation where they occur.
14. The method as claimed in claim 13, wherein weeds in crops are controlled selectively.
15. The method as claimed in claim 14, wherein the crop is one from the group comprising wheat, barley, rye, rice and maize.

* * * * *